United States Patent [19]

Ikeda et al.

[11] 4,355,532
[45] Oct. 26, 1982

[54] APPARATUS FOR TESTING DAMPING FORCES OF SHOCK ABSORBERS

[75] Inventors: Jun-ichi Ikeda, Tokyo; Yasuo Hasegawa, Sagamihara, both of Japan

[73] Assignee: Tokico Kabushiki Kaisha, Kanagawa, Japan

[21] Appl. No.: 199,518

[22] Filed: Oct. 22, 1980

[30] Foreign Application Priority Data

Oct. 23, 1979 [JP] Japan .................. 54-136843

[51] Int. Cl.³ .......................... G01M 17/04
[52] U.S. Cl. ............................ 73/11; 73/574
[58] Field of Search ............... 73/11, 574; 340/52 R

[56] References Cited

U.S. PATENT DOCUMENTS 4,103,532  8/1978  Buzzi ........................ 73/11
4,141,236  2/1979  Ellington .................. 73/11

FOREIGN PATENT DOCUMENTS 959933  6/1964  United Kingdom ............ 73/11
612155  6/1978  U.S.S.R. ..................... 73/11

*Primary Examiner*—James J. Gill
*Attorney, Agent, or Firm*—Quaintance & Murphy

[57] ABSTRACT

A damping force produced by a shock absorber being tested is detected and converted into an electric analog signal for deciding whether the damping force is acceptable or not. The shock absorber is mounted between a slider operatively connected to a motor for reciprocating movement and a free end of a load detection beam. A potentiometer and so on detect an amount of displacement of the free end of the load detection beam on reciprocation of the slider, and produces the electric analog signal for electrically deciding whether to accept the damping force tested of the shock absorber.

5 Claims, 5 Drawing Figures

4,355,532

APPARATUS FOR TESTING DAMPING FORCES OF SHOCK ABSORBERS

BACKGROUND OF THE INVENTION

1. Field of the Invention

The present invention relates to an apparatus for electrically testing shock absorbers for damping forces produced thereby in determining whether they are acceptable or not.

2. Prior Art

Shock absorbers have heretofore been tested for damping forces by detecting an amount of displacement of a load detection beam, which is a function of the damping force produced by the shock absorber while being compressed or extended. The amount of displacement of the beam is magnified by a lever and compared by visual inspection with a reference value in order to decide whether the damping force tested is allowable or not.

The prior procedure has been disadvantageous in that precise testing cannot be carried out.

SUMMARY OF THE INVENTION

A damping force produced by a shock absorber being tested is detected and converted into an electric analog signal that is utilized for electrically deciding whether to accept the damping force.

It is an object of the present invention to eliminate the prior art difficulty.

Another object of the present invention is to provide an apparatus for testing shock absorbers for damping forces reliably and with precision.

Other and further objects, features and advantages of the present invention will appear more fully from the following description when taken in conjunction with the accompanying drawings which show a preferred embodiment of the present invention by way of example.

DETAILED DESCRIPTION

Figure 1:
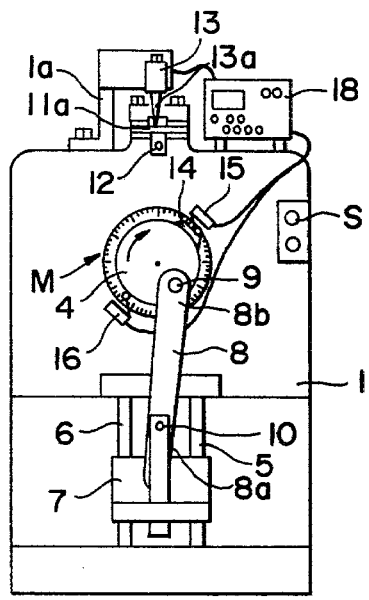
FIG. 1 is a front elevational view of an apparatus according to the present invention.
Figure 2:
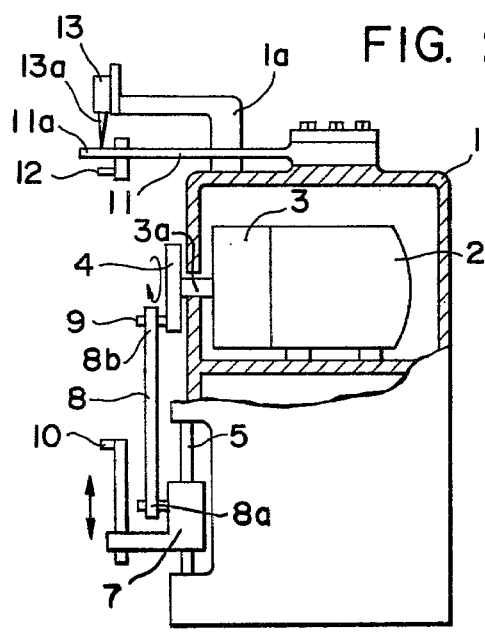
FIG. 2 is a side elevational view, partially in cross section, of the apparatus of FIG. 1.

In FIGS. 1 and 2, a motor 2 is mounted in a housing 1 and has an output shaft (not shown) coupled to a speed reducer 3 having an output shaft 3a to which a disc 4 is attached.

The housing 1 includes a pair of vertical guide rails 5, 6 on which a slider 7 is slidably supported for vertical sliding movement therealong. A connecting rod 8 has one or lower end 8a pivotally connected to the slider 7 and the other or upper end 8b pivotally connected to a pin 9 projecting from the disc 4 at an eccentric position thereon. While the eccentric drive has been shown, any known source of drive may be utilized which imparts reciprocating motion to the slider 7.

The slider 7 has a hook 10 for holding one end of a shock absorber (not shown) to be tested. A load detection beam 11 is mounted on an upper portion of the housing 1 in vertical correspondence to the hook 10, the beam 11 having a hook 12 on its free end 11a for holding the other end of the shock absorber. The housing 1 also includes a holder 1a supporting thereon a potentiometer 13 used as a displacement detector and having a measuring contact point 13a held against a free end 11a of the beam 11. The load detection beam 11 and the potentiometer 13 (displacement detector) jointly constitute a detector and converter for detecting a damping force generated by the shock absorber supported on the hooks 10, 12 as the slider 7 moves up and down and for converting the detected amount of displacement into an electric analog signal. While the potentiometer 13 has been described and shown as the displacement detector, the latter may be a differential transformer, a wire strain gauge or the like for use with the load detection beam 11. Where the wire strain gauge is employed, it may be associated with an amplifier.

A dog 14 is projectingly attached at a selected position to the periphery of the disc 4. A pair of limit switches 15, 16 are disposed adjacent to the disc 4 and each constitute a signal generator for generating a timing signal which indicates that the shock absorber is producing a damping force in which one of the extension or compression stroke. When the limit switch 15 is closed by the dog 14, a timing signal is generated which indicates the extension stroke of the shock absorber. Conversely, a timing signal indicative of the compression stroke is given off when the dog 14 closes the limit switch 16.

Figure 3:
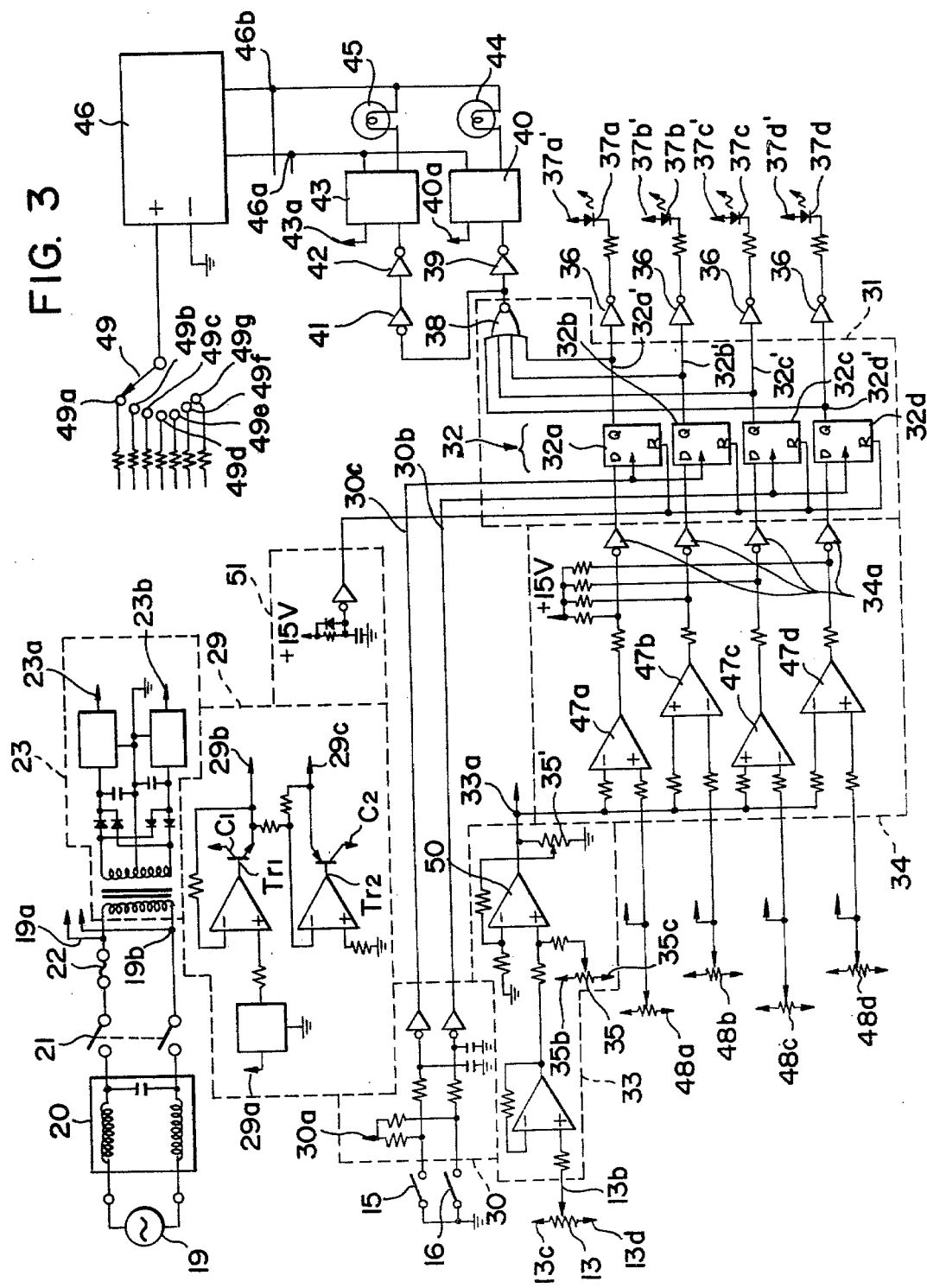
FIG. 3 is a circuit diagram of a decision indicator in the apparatus.

Designated at 18 in a decision indicator having an electric circuit as shown in FIG. 3. A power supply 19 is connected to a noise filter 20, and output side of the noise filter 20 is connected through a power supply switch 21 and a fuse 22 to a constant-voltage power supply circuit 23. The constant-voltage power supply circuit 23 has an output terminal 23a at a potential of +15 V and an output terminal 23b at a potential of −15 V.

A standard-voltage generator circuit 29 has an input terminal 29a connected to the output terminal 23a of the circuit 23. The circuit 29 includes a transistor $Tr_1$ having a collector $C_1$ connected to the output terminal 23a of the circuit 23 and a transistor $Tr_2$ having a collector $C_2$ connected to the output terminal 23b of the circuit 23. The circuit 29 has a pair of output terminals 29b, 29c on which there appear standard-voltages of +10 V and −10 V, respectively, based on the respective output voltages of +15 V and −15 V from the circuit 23.

The limit switches 15, 16 are connected to a waveform shaping circuit 30 having a noise filter and including a terminal 30a connected to the output terminal 23a of the circuit 23 and output terminals 30b, 30c connected to input terminals of a flip-flop circuit 32 in a decision circuit 31.

Figure 4:
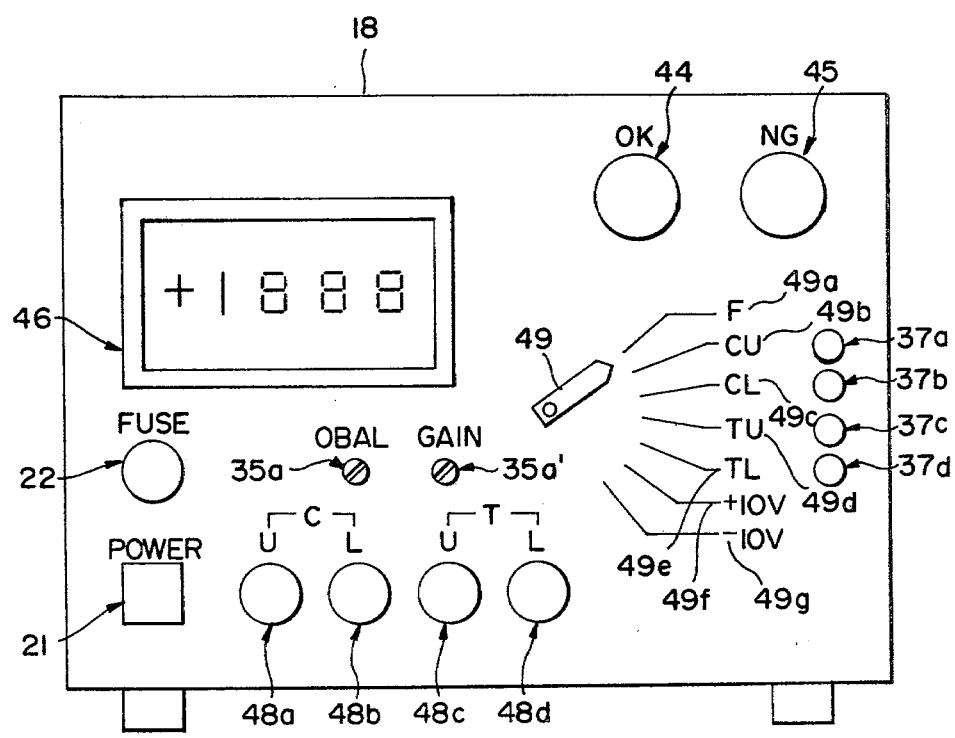
FIG. 4 is a front elevational view of the decision indicator.

The potentiometer 13 has an output terminal 13b coupled to an amplifier circuit 33 having an output terminal 33a connected to a comparator 34 with its output terminals 34a connected to input terminals of the flip-flop circuit 32. Designated at 35, 35′ are variable resistors for zero-balancing and gain adjustment of signals from the potentiometer 13, the resistors having knobs 35a, 35a′ (FIG. 4) accessible for adjustment on the indicator 18. The potentiometer 13 has a terminal 13c connected to the terminal 29b of the circuit 29, and a terminal 13d to the terminal 29c. The variable resistor 35 has a terminal 35b connected to the terminal 29b of the circuit 29, and a terminal 35c to the terminal 29c.

The flip-flop circuit 32 includes flip-flops 32a, 32b, 32c, 32d having output terminals 32a', 32b', 32c', 32d', respectively, connected via inverter buffers 36 respectively to indicator lamps 37a, 37b, 37c, 37d such for example as light emitting diodes (LED) or ordinary lamps. The indicator lamps 37a, 37b, 37c, 37d have terminals 37a', 37b', 37c', 37d' coupled to the terminal 23a of the circuit 23.

Each output terminal 32a', 32b', 32c', 32d' is connected via an OR gate 38 and an inverter buffer 39 to a solid-state relay 40 for converting signal levels from the flip-flops 32a, 32b, 32c, 32d into a signal level at AC 100 V. And each output terminal 32a', 32b', 32c', 32d' is also connected via inverter buffers 41, 42 to a solid-state relay 43 similar to the solid-state relay 40. The solid-state relays 40, 43 have terminals 40a, 43a, respectively, connected to the terminal 23a of the circuit 23. Series circuits comprising output terminals of the solid-state relays 40, 43 and lamps 44, 45 are connected, respectively, to a voltmeter 46, and input terminals 46a, 46b of the voltmeter 46 connected to terminals 19a, 19b from the power supply 19.

The comparator 34 includes operational amplifiers 47a, 47b, 47c, 47d having inputs connected respectively to variable resistors 48a, 48b, 48c, 48d connected between the terminals 29a, 29b of the circuit 29 and to contacts 49b, 49c, 49d, 49e of a rotary switch 49. The rotary switch 49 has a contact 49a connected to the output terminal 33a leading from an operational amplifier 50 in the amplifier circuit 33, a contact 49f connected to the terminal 29b of the circuit 29, and a contact 49g to the terminal 29c of the circuit 29.

The voltmeter 46 is indicative of the potential of a signal selected by the rotary switch 49.

Designated at 51 is an initially setting circuit for generating a reset signal to each flip-flop 32a, 32b, 32c, 32d of the decision circuit 31 when the power supply is switched on.

With such an arrangement, a shock absorber to be tested is first installed between the hook 12 on the beam 11 and the hook 10 on the slider 7. Then, the motor 2 is energized to drive the slider 7 up and down for thereby causing the shock absorber to be extended or compressed. As the disc 4 rotates, the limit switches 15, 16 are turned on or off to produce timing signals indicative of extension and compression of the shock absorber. A damping force produced by the shock absorber causes the beam 11 to flex, the amount of displacement of the latter being converted by the potentiometer 13 into an electric analog signal as a change in potential.

The amplifier circuit 33 is a circuit capable of changing the analog signal into a signal F (FIG. 5) which is proportional to the load applied to the shock absorber, the load signal F being available on a desired scale by adjustment of the variable resistor 35, 35' for zero-balancing and gain. For example, adjustment may be made for ±10 V with the load of ±100 Kg or ±10 V with the load of ±500 Kg. With the latter being the case, where a rated value is 100 Kg±10% for the damping force on compression stroke and 300 Kg±10% for the damping force on extension stroke, the voltage of an output signal CU from the variable resistor 48a for the upper limit of compression stroke should be adjusted to 10×(100×1.1)/500= +2.2 V, the voltage of an output signal CL from the variable resistor 48b for the lower limit of compression stroke to +1.8 V, the voltage of an output signal TU from the variable resistor 48c for the upper limit of extension stroke to −6.6 V, and the voltage of an output signal TL from the variable resistor 48d for the lower limit of extension stroke to −5.4 V. Thus the resistors 48a, 48b, 48c, 48d constitute a device for setting rated values.

These signal voltages for rated values are compared by the load signal F and the comparator 34 for being changed into a level of logic signals (ranging from 0 to +15 V in the illustrated embodiment).

Figure 5:
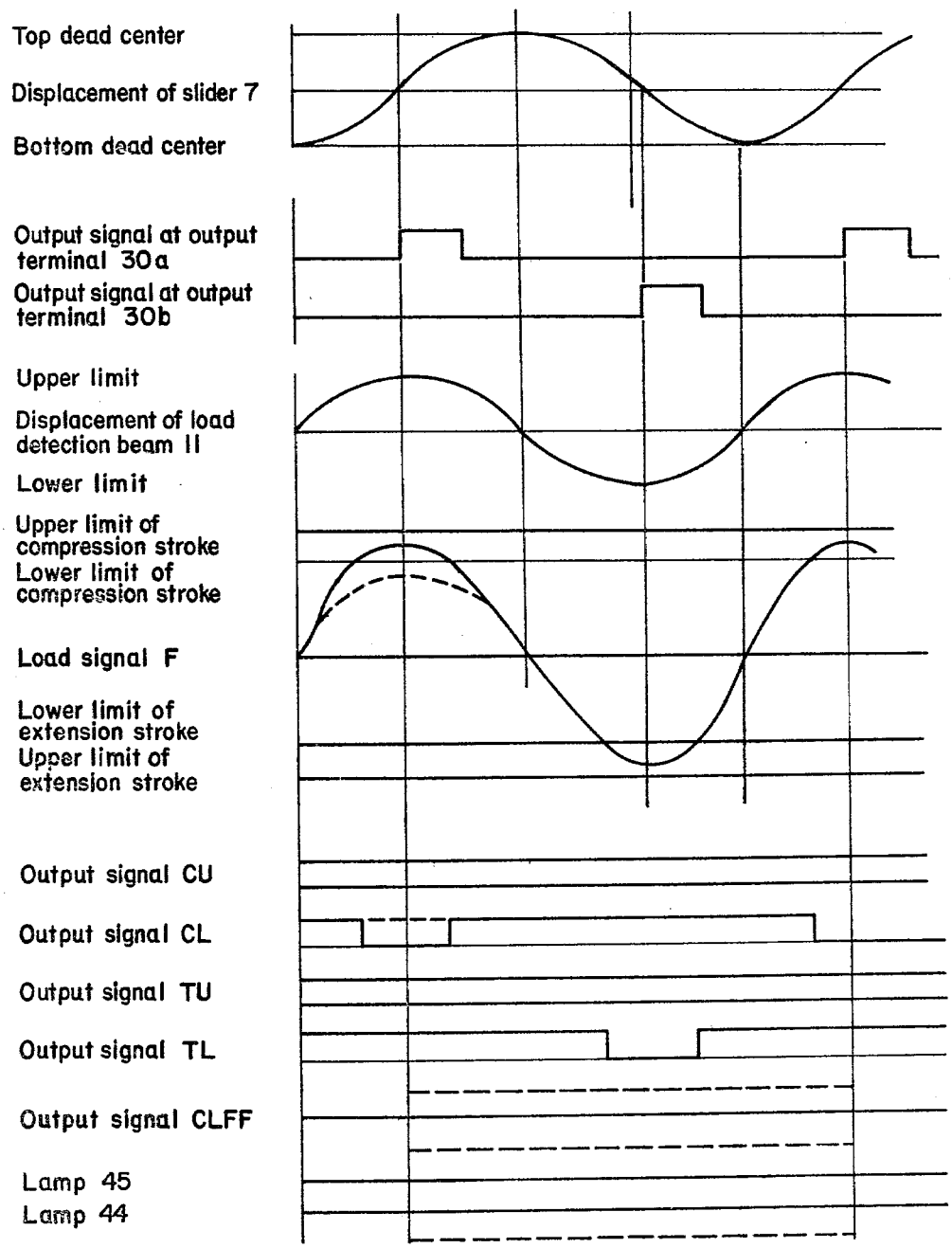
FIG. 5 is a time chart for various signals in the circuit shown in FIG. 3.

The decision of acceptance or unacceptance is made by holding the output of the comparator 34 with the rising of the output signal of the waveform shaping circuit 30 due to the data-type flip-flops 32a, 32b, 32c, 32d of the decision circuit 31 since the signal of the limit switches 15, 16 is generated from the waveform shaping circuit 30. In the illustrated embodiment, when the output of the flip-flops 32a, 32b, 32c, 32d are at H level, the damping force of the shock absorber being tested is not acceptable, and when outputs are at L level, the tested damping force is allowable. When all of the outputs of the flip-flops 32a, 32b, 32c, 32d are at the low level, the lamp 44 is turned on, and when any one of the outputs is at the high level, the lamp 45 is turned on. At the same time as the lamp 45 is energized, any one of the indicator lamps 37a, 37b, 37c, 37d is turned on which are indicative of unacceptable qualities (with respect to the damping forces at the upper limit of compression stroke, the lower limit of compression stroke, the upper limit of extension stroke, and the lower limit of extension stroke). The decision is made each time the dog 14 throws the limit switches 15, 16 on, so that the result is indicated at all times on the last one revolution of the disc 4 while the latter is rotating. Indicated by the broken lines in FIG. 5 are signals generated when the damping force on compression is off the rated value at the lower limit, and CLFF shows an output signal from the flip-flop 32d when the shock absorber is at the lower limit of compression stroke at that time.

To render the apparatus automatically operable, a mechanism may be provided for quickly de-energizing the motor 2 to stop the disc 4 substantially at a position of bottom dead center thereof upon completion of three revolutions of the disc 4 after turning on the starter switch S (FIG. 1), so as to allow the operator to install another shock absorber which can then be tested likewise by depressing the starter switch S. The housing 1 may be marked with angular graduations M arranged circumferentially around the disc 4 for easy repositioning of the limit switches to accommodate stroke changes.

The apparatus according to the present invention thus lends itself to precise testing of shock absorbers because of being able to electrically decide whether damping forces thereof are acceptable or not. The testing procedure can be automatically effected so that no skilled labor is required. Furthermore, outputs from the setting device for generating rated value signals and the converter for producing analog signals can easily be established by the voltmeter and at the same time, highly precise decision can be conducted.

Although a certain preferred embodiment has been shown and described in detail, it should be understood that many changes and modifications may be made therein without departing from the scope of the appended claims.

What is claimed is:

1. An apparatus for testing a shock absorber, wherein the shock absorber has first and second ends connected by a damping mechanism, and wherein the apparatus measures the damping forces of the damping mechanism during both the compression and extension strokes, the apparatus comprising:

a frame means for supporting the shock absorber;

first holding means for mounting the first end of the shock absorber on the frame means;

second holding means for mounting the second end of the shock absorber on the frame means;

means for reciprocating the first holding means with respect to the second holding means to compress and extend the shock absorber, said reciprocating means including:

a rotor member mounted on the frame means, for rotating the rotor member and means attached between the rotor and the first holding means for converting the rotation of the rotor member to reciprocating motion to thereby reciprocate the reciprocating means;

angular, position-sensing means juxtaposed between the rotor member and frame member for monitoring directly the angular position of the rotor member, said position-sensing means including means for generating a position signal indicative of the compression or extension of the shock absorber;

force detecting means attached to the second holding means for measuring the force imparted to the second holding means as the first holding means reciprocates with respect thereto, said force detecting means including analogue signal generating means for generating an analogue signal which is proportional to the force measured;

a monitoring circuit connected to both the position and analogue signal generator means for providing a periodic output signal during outer limits of the compression and extension strokes which output is indicative of the damping force at the outer limits of extension and compression;

reference circuit means for providing a reference signal indicative of desired levels of damping force at compression and extension of the shock absorber;

decision circuit means for comparing the output of the monitoring circuit with the reference signal, and means for indicating when the output of the monitoring circuit is less than the reference signal to thereby indicate whether the damping forces are within acceptable limits.

2. The apparatus according to claim 1 wherein the decision circuit includes a flip-flop circuit for retaining the position signal and wherein the indicating means includes lamp means which light to indicate acceptance or rejection of the shock absorber.

3. The apparatus of claim 1 wherein the angular position-sensing means includes a pair of limit switches circumferentially positionable with respect to the rotor and spaced from one another and spaced trip means on the rotor for operating the limit switches.

4. The apparatus according to claim 3 wherein the rotor includes angular graduations marked circumferentially therearound to facilitate convenient adjustment of the position of the limit switches.

5. The apparatus of claim 3 further including a motor for driving the rotor and angular graduations marked around the rotor to facilitate positioning of the limit switches, and wherein the means for converting rotation of the rotor to reciprocating motion includes a crank arm attached to the rotor and a slide attached to the crank arm, the slide being attached to the first holding means for reciprocating the first holding means as the rotor rotates.

* * * * *